(12) United States Patent
Ko et al.

(10) Patent No.: US 7,018,497 B2
(45) Date of Patent: Mar. 28, 2006

(54) METHOD OF MAKING AN ABSORBENT STRUCTURE HAVING HIGH INTEGRITY

(75) Inventors: Young C. Ko, Neenah, WI (US); Kambiz B. Makoui, Neenah, WI (US); Richard H. Thiessen, Appleton, WI (US); Jason M. Laumer, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 202 days.

(21) Appl. No.: 10/409,945

(22) Filed: Apr. 9, 2003

(65) Prior Publication Data

US 2003/0205318 A1    Nov. 6, 2003

Related U.S. Application Data

(63) Continuation-in-part of application No. 10/017,760, filed on Dec. 14, 2001, now Pat. No. 6,918,981.

(51) Int. Cl.
*B05D 1/36* (2006.01)

(52) U.S. Cl. .............. 156/181; 156/277; 156/279; 427/337; 427/392; 427/393; 427/407.1; 264/109; 264/122

(58) Field of Classification Search .......... 156/62.2, 156/180, 181, 277, 279; 427/392, 393, 331, 427/337, 407.1; 264/109, 122
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,901,236 A | 8/1975 | Assarsson et al. | |
| 4,076,663 A | 2/1978 | Masuda et al. | |
| 4,100,324 A | 7/1978 | Anderson et al. | |
| 4,151,130 A | 4/1979 | Adams | 260/17.4 GC |
| 4,286,082 A | 8/1981 | Tsubakimoto et al. | |
| 4,340,563 A | 7/1982 | Appel et al. | |
| 4,500,315 A | 2/1985 | Pieniak et al. | |
| 4,537,590 A | 8/1985 | Pieniak et al. | |
| 4,540,454 A | 9/1985 | Pieniak et al. | |
| 4,559,050 A | 12/1985 | Iskra | |
| 4,560,372 A | 12/1985 | Pieniak | |

(Continued)

FOREIGN PATENT DOCUMENTS

DE    199 05 947 A1    8/2000

(Continued)

*Primary Examiner*—Sam Chuan Yao
(74) *Attorney, Agent, or Firm*—Pauley Petersen & Erickson (57) ABSTRACT

A method of making an absorbent structure having high integrity is provided. A first superabsorbent polymer precursor composition including a monomer, a crosslinking agent and a reducing agent, and a second superabsorbent polymer precursor composition including a monomer, a crosslinking agent and an oxidizing agent are combined at a plurality of discrete, spaced-apart locations on or in a substrate. The precursor compositions react with each other to form discrete, spaced-apart microdomains of superabsorbent polymer adhering to the substrate. The spacing is sufficient to avoid gel blocking when the microdomains swell due to liquid absorption. The adhesion to the substrate is sufficient to maintain spacings between the microdomains of superabsorbent polymer.

27 Claims, 4 Drawing Sheets

U.S. PATENT DOCUMENTS

| | | |
|---|---|---|
| 4,596,567 A | 6/1986 | Iskra |
| 4,605,402 A | 8/1986 | Iskra |
| 4,676,784 A | 6/1987 | Erdman et al. |
| 4,699,823 A | 10/1987 | Kellenberger et al. |
| 4,818,464 A | 4/1989 | Lau |
| 4,888,238 A | 12/1989 | Katz et al. ................... 428/378 |
| 4,892,754 A | 1/1990 | Itoh et al. |
| 4,902,559 A | 2/1990 | Eschwey et al. |
| 4,958,385 A | 9/1990 | Rushton, Jr. .................... 2/174 |
| 5,059,664 A | 10/1991 | Yada et al. ................. 526/240 |
| 5,071,681 A | 12/1991 | Manning et al. ............ 427/392 |
| 5,175,046 A | 12/1992 | Nguyen ...................... 428/198 |
| 5,248,524 A | 9/1993 | Soderlund ................... 427/200 |
| 5,298,284 A | 3/1994 | Buckwald et al. .......... 427/203 |
| 5,300,565 A | 4/1994 | Berg et al. ................. 525/54.2 |
| 5,350,624 A | 9/1994 | Georger et al. |
| 5,422,169 A | 6/1995 | Roe |
| 5,454,801 A | 10/1995 | Lauritzen .................... 604/378 |
| 5,487,736 A | 1/1996 | Van Phan ................... 604/368 |
| 5,489,469 A | 2/1996 | Kobayashi et al. ......... 428/283 |
| 5,506,035 A | 4/1996 | Van Phan et al. .......... 428/196 |
| 5,547,747 A | 8/1996 | Trokhan et al. |
| 5,549,928 A | 8/1996 | Trokham et al. ............ 427/625 |
| 5,620,742 A | 4/1997 | Lauritzen .................... 427/209 |
| 5,674,478 A | 10/1997 | Dodd et al. |
| 5,817,081 A | 10/1998 | LaVon et al. |
| 5,821,179 A | 10/1998 | Masaki et al. |
| 5,868,724 A | 2/1999 | Dierckes, Jr. et al. ...... 604/368 |
| 5,875,967 A | 3/1999 | Ruth, III |
| 5,962,068 A | 10/1999 | Tsuchiya et al. |
| 5,998,312 A * | 12/1999 | Kroesbergen ............... 442/221 |
| 6,019,457 A | 2/2000 | Silverbrook |
| 6,022,610 A | 2/2000 | Phan et al. .................. 428/171 |
| 6,024,438 A | 2/2000 | Koike et al. |
| 6,043,311 A | 3/2000 | Houben et al. ............. 524/522 |
| 6,086,950 A | 7/2000 | Masaki et al. |
| 6,103,061 A | 8/2000 | Anderson et al. |
| 6,235,659 B1 | 5/2001 | McAmish et al. ............ 442/79 |
| 6,242,073 B1 | 6/2001 | Phan et al. .................. 428/132 |
| 6,417,425 B1 | 7/2002 | Whitmore et al. |
| 6,533,989 B1 | 3/2003 | Wisneki et al. |
| 2003/0149413 A1 | 8/2003 | Mechawej ................... 604/368 |
| 2003/0205318 A1 | 11/2003 | Ko et al. |
| 2003/0211248 A1 | 11/2003 | Ko et al. |

FOREIGN PATENT DOCUMENTS

| | | |
|---|---|---|
| EP | 0 022 792 B1 | 5/1984 |
| EP | 0 290 814 A2 | 11/1988 |
| EP | 0 301 804 A2 | 2/1989 |
| EP | 0 301 804 A3 | 5/1990 |
| EP | 0 390 513 A2 | 10/1990 |
| EP | 0 402 650 A2 | 12/1990 |
| EP | 0 390 513 A3 | 8/1991 |
| EP | 0 402 650 A3 | 11/1991 |
| EP | 0 223 908 B1 | 2/1993 |
| EP | 719 531 | 7/1996 |
| EP | 0 729 336 B1 | 6/1998 |
| EP | 729 336 | 6/1998 |
| EP | 0 992 250 A2 | 4/2000 |
| EP | 1 142 696 A1 | 10/2001 |
| EP | 1 178 149 A1 | 2/2002 |
| WO | 95/13778 | 5/1995 |
| WO | WO 95/13777 | 5/1995 |
| WO | WO 95/13778 | 5/1995 |
| WO | WO 96/23024 | 8/1996 |
| WO | 98/51251 | 11/1998 |
| WO | WO 99/34041 | 7/1999 |
| WO | 00/55418 | 9/2000 |
| WO | 01/23177 | 4/2001 |
| WO | WO 01/31123 A1 | 5/2001 |
| WO | WO 01/56625 A2 | 8/2001 |
| WO | WO 01/56625 A3 | 8/2001 |
| WO | WO 02/053363 A2 | 7/2002 |
| WO | WO 03/051253 A1 | 6/2003 |
| WO | WO 03/051945 A1 | 6/2003 |

* cited by examiner

METHOD OF MAKING AN ABSORBENT STRUCTURE HAVING HIGH INTEGRITY

This application is a continuation-in-part of U.S. patent application Ser. No. 10/017,760, filed on Dec. 14, 2001 now U.S. Pat. No. 6,918,981.

FIELD OF THE INVENTION

1. Field of the Invention

This invention relates to a method of making an absorbent structure having high structural integrity.

2. Background of the Invention

Processes for making absorbent composite materials having a superabsorbent polymer component are known. In various processes, preformed superabsorbent polymer particles or fibers are combined with cellulose fibers, thermoplastic fibers and the like in a web formation process to make a composite web structure. Illustrative processes are disclosed in U.S. Pat. No. 4,818,464 to Lau, U.S. Pat. No. 4,100,324 to Anderson et al., U.S. Pat. No. 5,350,624 to Georger et al., and U.S. Pat. No. 4,902,559 to Eschwey et al. These processes are commonly referred to as "coform" processes.

Additionally, a process is known where a superabsorbent polymer is only partially formed from a precursor monomer before being added to a fibrous substrate, and the polymerization is completed after the partially polymerized monomer contacts the substrate. U.S. Pat. No. 5,962,068 to Tsuchiya et al. discloses a water-absorptive composite including a fibrous substrate and water-absorptive polymer particles. The water-absorptive polymer precursor is partially polymerized with the aid of a redox initiator before being added to the fibrous substrate. The partially polymerized material is added in a dropwise fashion in a single stream to the substrate, and the polymerization reaction then proceeds to completion.

One feature that the known processes have in common, is that they require at least some separate process steps for polymerizing or partially polymerizing the superabsorbent material before it can be added to the fibrous substrate. In other words, neither process totally forms the superabsorbent polymer within the fibrous substrate.

DEFINITIONS

The term "cellulose fibers" refers to fibers from natural sources such as woody and non-woody plants, regenerated cellulose, and the derivatives from these fibers by means of chemical, mechanical, thermal treatment, or any combination of these. Woody plants include, for example, deciduous and coniferous trees. Non-woody plants include, for instance, cotton, flax, esparto grass, milkweed, straw, jute hemp, and bagasse. Regenerated cellulose fibers include, for instance, viscose and rayon. The cellulose derivatives include, for instance, microcrystalline cellulose, chemically crosslinked fibers, and un-crosslinked, twisted fibers.

The term "average fiber length" refers to a weighted average length of fiber determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k} (X_i * n_i)/n$$

where k=maximum fiber length, $X_i$=individual fiber length, $n_i$=number of fibers having length $X_i$ and n=total number of fibers measured.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "staple filaments or fibers" means filaments or fibers which are natural or which are cut from a manufactured filament prior to forming into a web, and which have a length ranging from about 0.1 to about 15 cm, more commonly about 0.2 to about 7 cm.

The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "substantially continuous filaments or fibers" refers to filaments or fibers prepared by extrusion from a spinnerette, including without limitation spunbonded and meltblown fibers, which are not cut from their original length prior to being formed into a fibrous web. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a fibrous web, but which are later cut when the nonwoven web or fabric is cut.

The term "nonwoven web" means a web having a structure of fibers or filaments which are interlaid, but not in an identifiable manner as in a knitted fabric. "Fibrous" webs include nonwoven webs as well as webs where the fibers are interlaid in an identifiable (e.g., regular) manner. The terms "fiber" and "filament" are used herein interchangeably. Nonwoven webs have been formed from many processes such as, for example, meltblowing processes, spunbonding processes, air laying processes, and bonded carded web processes. The term also includes films that have been perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.) The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "wettable" and/or "hydrophilic" is meant to refer to a fiber which exhibits a liquid such as water, synthetic urine, or a 0.9 weight percent aqueous saline solution, in air contact angle of less than 90 degrees. The contact angle may be determined, for example, in accordance with ASTM D724-89.

The term "thermoplastic" is meant to describe a material that softens and flows when exposed to heat and which substantially returns to its original hardened condition when cooled to room temperature.

The term "superabsorbent polymer precursor composition" refers to any and all solutions which, when mixed, chemically react to form a superabsorbent polymer. Each solution may be comprised of any combination of oligomer(s), monomer(s), crosslinking reagent(s), neutralizing agent, or initiator(s). In instances when only a single solution is utilized all the desired components must be in said solution and the initiator(s) must require a later activation step (e.g., heating or irradiation). In instances when two or more solutions are utilized the initiator(s) is most often, but not limited to, a chemical redox pair. When a redox pair, comprised of an oxidizing radical generator and a reducing agent, is used as the initiator the oxidizing radical generator and reducing agent must be in separate solutions. The solution of oxidizing radical generator or reducing agent may also contain any combination of oligomer(s), monomers(s), crosslinking reagent(s), or neutralizing agent.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 50 percent greater than its relaxed unbiased length, and that will cause the material to recover at least 40 percent of its elongation upon release of the stretching elongating force. A hypothetical example which would satisfy this definition of an elastomenrc material would be a one (1) inch sample of a material which is elongatable to at least 1.50 inches and which, upon being elongated to 1.50 inches and released, will recover to a length of not more than 1.30 inches. Many elastic materials may be stretched by much more than 50 percent of their relaxed length, and many of these will recover to substantially their original relaxed length upon release of the stretching, elongating force.

The term "recover" or "retract" relates to a contraction of a stretched material upon termination of a biasing force following stretching of the material by application of the biasing force.

The term "superabsorbent material" refers to a water swellable, water-insoluble organic or inorganic material capable, under the most favorable conditions, of absorbing at least about 10 times its weight, preferably at least about 20 times its weight in an aqueous solution containing 0.9% by weight sodium chloride. The term "absorbent material" refers to any material capable of absorbing at least about 5 times its weight of the aqueous solution under the same conditions.

The term "personal care absorbent article" includes diapers, training pants, swim wear, absorbent underpants, adult incontinence products, feminine hygiene products, and the like.

The term "medical absorbent article" includes medical absorbent garments, drapes, gowns, bandages, wound dressings, underpads, wipes, and the like.

The term "tissue and towel article" includes facial and bathroom tissue, paper towels, wet wipes, and the like.

SUMMARY OF THE INVENTION

The present invention is directed to a method for making an absorbent structure having high integrity due to fixed locations of superabsorbent material on or in a substrate. A first superabsorbent polymer precursor composition is prepared which includes a monomer, a crosslinking agent and a reducing agent. A second superabsorbent polymer precursor composition is prepared which includes a monomer, a crosslinking agent and an oxidizing agent. The first and second superabsorbent polymer precursor compositions are delivered to the same locations on or in the substrate simultaneously or in different steps. The precursor compositions are delivered to a plurality of locations, which are discrete and spaced-apart. The substrate may be a fibrous web, a foam scrim, or another suitable material.

Once the first and second superabsorbent polymer precursor compositions contact each other on or in the substrate, they polymerize to form a plurality of discrete microdomains of superabsorbent polymer on or in the substrate. The microdomains are spaced apart, so that when they swell due to contact with a liquid, there is sufficient spacing to prevent gel blocking. The in situ polymerization results in domains formed on or around individual fibers or other substrate components with sufficient adhesion to alleviate or prevent migration of the superabsorbent polymer domains.

The superabsorbent polymer precursor compositions may be added at spaced-apart locations to the substrate using contact printing processes, including without limitation screen printing and gravure printing. The superabsorbent polymer precursor compositions may also be added at spaced-apart locations using non-contact printing processes, including without limitation dropwise addition. The first superabsorbent polymer precursor may be added at spaced-apart locations to the substrate using a contact printing process, including without limitation screen printing and gravure printing while the second superabsorbent polymer precursor may be added at spaced-apart locations using a non-contact printing process, including without limitation spraying or inkjet printing. Likewise, the first superabsorbent polymer precursor may be added at spaced-apart locations using a non-contact printing process, including without limitation spraying or inkjet printing while the second superabsorbent polymer precursor may be added at spaced-apart locations using a contact printing process, including without limitation screen printing and gravure printing.

The first and second superabsorbent polymer precursor compositions are added separately, meaning they are not mixed together or otherwise in contact with each other before being added to the substrate. The monomer(s), crosslinking agent(s), oxidizing and reducing agents are selected so that the polymerization reaction for making superabsorbent polymer proceeds spontaneously on or in the substrate, when the precursor compositions contact each other.

The resulting absorbent structure has excellent intake, absorption and distribution of fluids, particularly aqueous liquids, due to the controlled size and spacing between the superabsorbent polymer domains.

DETAILED DESCRIPTION OF THE PRESENTLY PREFERRED EMBODIMENTS

In accordance with the invention, a pre-formed substrate is provided. The substrate may be a fibrous web, a foam scrim, or another suitable material. The substrate may be a nonwoven web, for instance, which contains about 25 to about 100% by weight of absorbent and/or other hydrophilic fibers and zero to about 75% by weight of thermoplastic fibers, suitably about 50 to about 100% by weight absorbent and/or other hydrophilic fibers and zero to about 50% by weight thermoplastic fibers, desirably about 60 to about 90% by weight absorbent and/or other hydrophilic fibers and about 10 to about 40% by weight thermoplastic fibers. The substrate (e.g., nonwoven web) may be formed using any conventional technique.

Desirably, the hydrophilic fibers include cellulose fibers. Examples of cellulose fibers include without limitation wood pulp fibers, wood pulp fluff, curled pulp fibers, microcrystalline cellulose, microfibrillar cellulose, cotton, and the like. Other hydrophilic fibers may also be employed, as well as absorbent staple fibers. Pre-formed superabsorbent particles or fibers may also be included. However, for purposes of the invention, at least some superabsorbent polymer must be formed in situ as described below.

When thermoplastic fibers are employed, they may include meltblown fibers. The meltblown fibers may be formed from thermoplastic polymers including, without limitation, polyolefins, polyamides, polyester, polyurethane, polyvinyl alcohol, polycaprotactone, styrene butadiene block copolymers or the like. Suitable polyolefins include without limitation polyethylene, polypropylene, polybutylene, copolymers of ethylene with other alpha-olefins, copolymers of propylene with other alpha-olefins, copolymers of butylene with other alpha-olefins, and combinations thereof. Processes for forming absorbent nonwoven webs containing hydrophilic fibers, meltblown fibers, and other optional ingredients are disclosed in U.S. Pat. No. 5,350,624 to Georger et al.; U.S. Pat. No. 4,818,464 to Lau; and U.S. Pat. No. 4,100,324 to Anderson et al.; the disclosures of which are incorporated by reference.

When thermoplastic polymers are employed, they may include spunbond fibers formed from any of the thermoplastic polymers listed above as being useful for meltblown fibers. A process for forming absorbent nonwoven webs containing hydrophilic fibers, spunbond fibers, and other optional ingredients is disclosed in U.S. Pat. No. 4,902,559 to Eschwey et al., the disclosure of which is incorporated by reference.

In accordance with the invention, a first superabsorbent polymer precursor composition and a second superabsorbent polymer precursor composition are applied to the substrate in different streams, at the same or different times. The first and second precursor compositions are applied to the same locations on or in the substrate, at the same or different times. The locations are discrete and spaced apart. The locations where the first and second precursor compositions are applied may have an average diameter of about 10 to about 1000 microns, particularly about 50 to about 800 microns, particularly about 100 to about 500 microns. The locations of application may be spaced apart from each other by an average of about 30 to about 3000 microns, particularly about 150 to about 2500 microns, particularly about 300 to about 1500 microns.

The first superabsorbent polymer precursor composition includes a monomer, a crosslinking agent and a reducing agent. The second superabsorbent polymer precursor composition includes a monomer, a crosslinking agent and an oxidizing agent. The monomer in the second superabsorbent polymer precursor composition may be the same as the monomer in the first superabsorbent polymer precursor composition, or may be a different monomer which is copolymerizable with the monomer in the first superabsorbent polymer precursor composition.

A wide variety of superabsorbent-forming monomers may be employed in the first and second superabsorbent polymer precursor compositions. Suitable superabsorbent-forming monomers include the following monomers, and combinations thereof 1. Carboxyl group-containing monomers: monoethylenically unsaturated mono or poly-carboxylic acids, such as (meth)acrylic acid (meaning acrylic acid or methacrylic acid. Similar notations are used hereinafter), maleic acid, fumaric acid, crotonic acid, sorbic acid, itaconic acid, and cinnamic acid;

2. Carboxylic acid anhydride group-containing monomers: monoethylenically unsaturated polycarboxylic acid anhydrides (such as maleic anhydride);

3. Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate, sodium maleate, methylamine maleate);

4. Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

5. Sulfonic acid salt group-containing monomers: alkali metal salts, ammonium salts, amine salts of sulfonic acid group containing monomers as mentioned above;

6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth)acrylate, triethylene glycol (meth)acrylate, poly(oxyethylene oxypropylene) glycol mono (meth)allyl ether (in which hydroxyl groups may be etherified or esterified);

7. Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], vinyl lactams (such as N-vinylpyrrolidone);

8. Amino group-containing monomers: amino group-containing esters (e.g., dialkylaminoalkyl esters, dihydroxyalkylaminoalkyl esters, morpholinoalkyl esters, etc.) of monoethylenically unsaturated mono-or di-carboxylic acid [such as dimethlaminoethyl (meth)acrylate, diethylaminoethyl (meth)acrylate, morpholinoethyl (meth)acrylate, dimethyl aminoethyl fumarate], heterocyclic vinyl compounds [such as vinyl pyridines (e.g., 2-vinyl pyridine, 4-vinyl pyridine, Nvinyl pyridine), N-vinyl imidazol]; and 9. Quaternary ammonium salt group-containing monomers: N,N,Ntrialkyl-N-(meth)acryloyloxyalkylammonium salts [such as N,N,N-trimethyl-N-(meth)acryloyloxyethylammonium chloride, N,N,N-triethyl-N-(meth)acryloyloxyethylamonnium chloride, 2-hydroxy-3-(meth)-acryloyloxypropyl trimethyl ammonium chloride].

10. Ether-group containing monomers: methoxy polyethylene glycol (meth)acrylate; polyethylene glycol dimethacrylate.

Particular superabsorbent-forming monomers suitable for the process of the invention include without limitation aliphatic unsaturated monocarboxylic acids or salts thereof; specifically unsaturated monocarboxylic acids or salts thereof such as acrylic acid or salts thereof, methacrylic acid or salts thereof, or unsaturated dicarboxylic acids or salts thereof such as maleic acid or salts thereof, itaconic acid or salts thereof, which may be used alone or in combination.

Among these, acrylic acid or salts thereof and methacrylic acid or salts thereof are useful, especially acrylic acid or salts thereof. An acrylic acid which is 50 mole % neutralized using aqueous sodium hydroxide or another suitable base, as explained below, is particularly useful.

Polymerizable monomers giving a water-absorbing polymer in the present invention are suitably aliphatic unsaturated carboxylic acids or salts thereof as described above, therefore, aqueous solutions of these polymerizable monomers are suitably aqueous solutions essentially containing an aliphatic unsaturated carboxylic acid or a salt thereof. As used here, the expression "essentially containing an aliphatic unsaturated carboxylic acid or a salt thereof" means that the aliphatic unsaturated carboxylic acid or a salt thereof is contained at about 50 mol % or more, suitably about 80 mol % or more on the basis of the total amount of the polymerizable monomer.

Suitable salts of aliphatic unsaturated carboxylic acids normally include water-soluble salts such as alkali metal salts, alkali earth metal salts, ammonium salts or the like. The neutrality is appropriately selected depending on the purpose, but 20–90 mol % of carboxyl group is suitably neutralized with an alkali metal salt or an ammonium salt in the case of acrylic acid. If the partial neutrality of an acrylic monomer is less than 20 mol %, the resulting water-absorbing polymer tends to have low water-absorbing capacity.

Acrylic monomers can be neutralized with alkali metal hydroxides or bicarbonates or ammonium hydroxide or the like, preferably alkali metal hydroxides such as, sodium hydroxide and potassium hydroxide.

Superabsorbent-forming monomers may also include comonomers which are polymerizable along with any of the monomers listed above. The comonomers may form part of the same superabsorbent polymer precursor composition as the primary monomer, or may be part of a different superabsorbent polymer precursor composition. While it may be desirable in some instances to add comonomers in different superabsorbent polymer precursor compositions, they may be added in the same precursor composition as the primary monomer if the primary monomer and comonomer will not spontaneously react with each other. Where the primary monomer is an aliphatic unsaturated carboxylic acid, suitable comonomers include without limitation secondary monomers such as (meth)acrylamide, (poly)ethylene glycol (meth)acrylate, 2-hydroxyethyl (meth)acrylate or even slightly water-soluble monomers including acrylate capped urethanes, acrylic alkyl esters such as methyl acrylate or ethyl acrylate may also be copolymerized in an amount within a range that does not affect performance of the resulting water-absorbing polymers in the present invention. As used herein, the term "(meth)acryl" means both "acryl" and "methacryl."

A crosslinking agent ("crosslinker") is also present in the first superabsorbent polymer precursor composition and in the second superabsorbent polymer precursor composition. The crosslinker generally improves the water-absorbing performance of the resulting superabsorbent polymer. The crosslinker used in the first superabsorbent polymer precursor composition may be the same or different as the crosslinker used in the second superabsorbent polymer precursor composition. The crosslinker(s) may be present in the first and second superabsorbent polymer precursor compositions at about 0.001 to about 1% by weight, particularly about 0.01 to about 0.5% by weight, based on the weight of the monomer(s).

Useful crosslinkers include divinyl compounds copolymerizable with the monomer(s) such as N,N'-methylenebis (meth)acrylamide, (poly)ethylene glycol di(meth)acrylate and water-soluble compounds having two or more functional groups capable of reacting with a carboxylic acid including polyglycidyl ethers such as ethylene glycol diglycidyl ether, and polyethylene glycol diglycidyl ether. Among them, N,N'-methylenebis (meth)acrylamide is particularly useful.

The first superabsorbent polymer precursor composition also includes a reducing agent. The reducing agent should be capable of forming a redox system with the oxidizing agent in the second superabsorbent polymer precursor composition. The reducing to agent may be present at about 0.001 to about 10% by weight, suitably about 0.01 to about 2% by weight, based on the weight of the superabsorbent-forming monomer in the first precursor composition. Suitable reducing agents include sulfites such as sodium sulfite or sodium hydrogensulfite, sodium thiosulfate, cobalt acetate, copper sulfate, ferrous sulfate, ferrous ammonium sulfate, sodium metabisulfite, tertiary amines or diamines, L-ascorbic acid or L-ascorbic acid alkali metal salts, etc. Among others, L-ascorbic acid or L-ascorbic acid alkali metal salts are particularly suitable.

The second superabsorbent polymer precursor composition also includes an oxidizing agent. The oxidizing agent should be capable of forming a redox system with the reducing agent in the first superabsorbent polymer precursor composition. The oxidizing agent may be present at about 0.001 to about 10% by weight, suitably about 0.01 to about 2% by weight, based on the weight of the superabsorbent-forming monomer in the second precursor composition. Suitable oxidizing agents include hydrogen radical generator and a reducing agent. Such oxidizing agents include hydrogen peroxide, potassium bromate, N-bromosuccinimide, persulfates such as ammonium persulfate, sodium persulfate, or potassium persulfate, peroxides including hydroperoxides such as 1-butyl hydroperoxide or cumene hydroperoxide, secondary cerium salts, permanganates, chlorites, hypochlorites, etc., among which hydrogen peroxide is particularly suitable.

The first and second superabsorbent polymer precursor compositions may be provided in an organic or inorganic solvent, suitably water. The concentration of polymerizable monomer(s) in an aqueous polymerizable monomer solution essentially containing an aliphatic unsaturated carboxylic acid or a salt thereof as described above is about 20% or more, particularly about 25% or more. Concentrations less than about 20% by weight are less desirable because excessive dilution may cause the resulting water-absorbing polymer to be applied too thinly, resulting in insufficient water-absorbing capacity. The monomer concentration may range up to about 80% by weight in respect of handling of the polymerization reaction solution. A viscosity modifier and/or surfactant may also be added to the solution.

The first and second superabsorbent polymer precursor compositions may be applied to the substrate using a variety of processes, provided that care is taken to apply the first and second precursor compositions in the same locations, without combining the first and second precursor compositions before they contact the substrate. If the first and second precursor compositions are applied to the substrate at different locations, they may not combine or react with each other to form domains of superabsorbent polymer. If the first and second precursor compositions are combined with each other before they contact the substrate, the advantages of in situ superabsorbent polymer formation may be lost to the extent that a superabsorbent polymer is formed apart from the substrate. The advantages of in situ superabsorbent polymerization are best achieved when a) the first and second superabsorbent polymer precursor compositions first contact each other at about the same time that they first contact the substrate, or b) one of the superabsorbent polymer precursor compositions is first applied to the substrate, then the other is applied at the same locations.

The first and second superabsorbent polymer precursor compositions may be applied to the substrate using a contact printing process. The use of gravure rolls for contact printing is described in U.S. Pat. No. 5,549,928 to Trokhan et al., and U.S. Pat. No. 6,022,610 to Phan et al., the disclosures of which are incorporated by reference. In one embodiment, two identical gravure printing rolls can be provided in series, with their motion synchronized so that they print the fibrous web substrate at precisely the same spaced-apart locations. The substrate passes the first gravure printing roll, which is used to apply one of the first and second precursor compositions at discrete, spaced-apart locations. Then, the substrate passes the second gravure printing roll, which is used to apply the other of the first and second precursor compositions at the same discrete, spaced-apart locations. The first and second precursor compositions react with each other immediately following the second application, to form discrete microdomains of the superabsorbent polymer on or in the substrate.

In another embodiment, only one gravure printing roll maybe used to apply the first and second precursor compositions. The first and second precursor compositions may be applied through openings in the gravure printing roll which are immediately adjacent to each other, or which converge at the surface of the printing roll so that the first and second precursor compositions are combined just as they are being applied to the substrate.

The first and second superabsorbent polymer precursor compositions may also be applied using a screen printing process or a non-contact printing process such as dropwise addition. In either case, the process must be adapted so that the first and second precursor compositions contact each other at discrete, spaced-apart locations on or in the substrate, and do not significantly contact or react with each other before reaching the substrate. In another embodiment, only one of the precursor compositions may be printed onto the substrate at discrete, spaced-apart locations. The other precursor composition may then be sprayed, brushed or otherwise applied to the substrate, whereupon polymerization will occur only in some or all of the spaced-apart locations occupied by the printed precursor composition.

Figure 1:
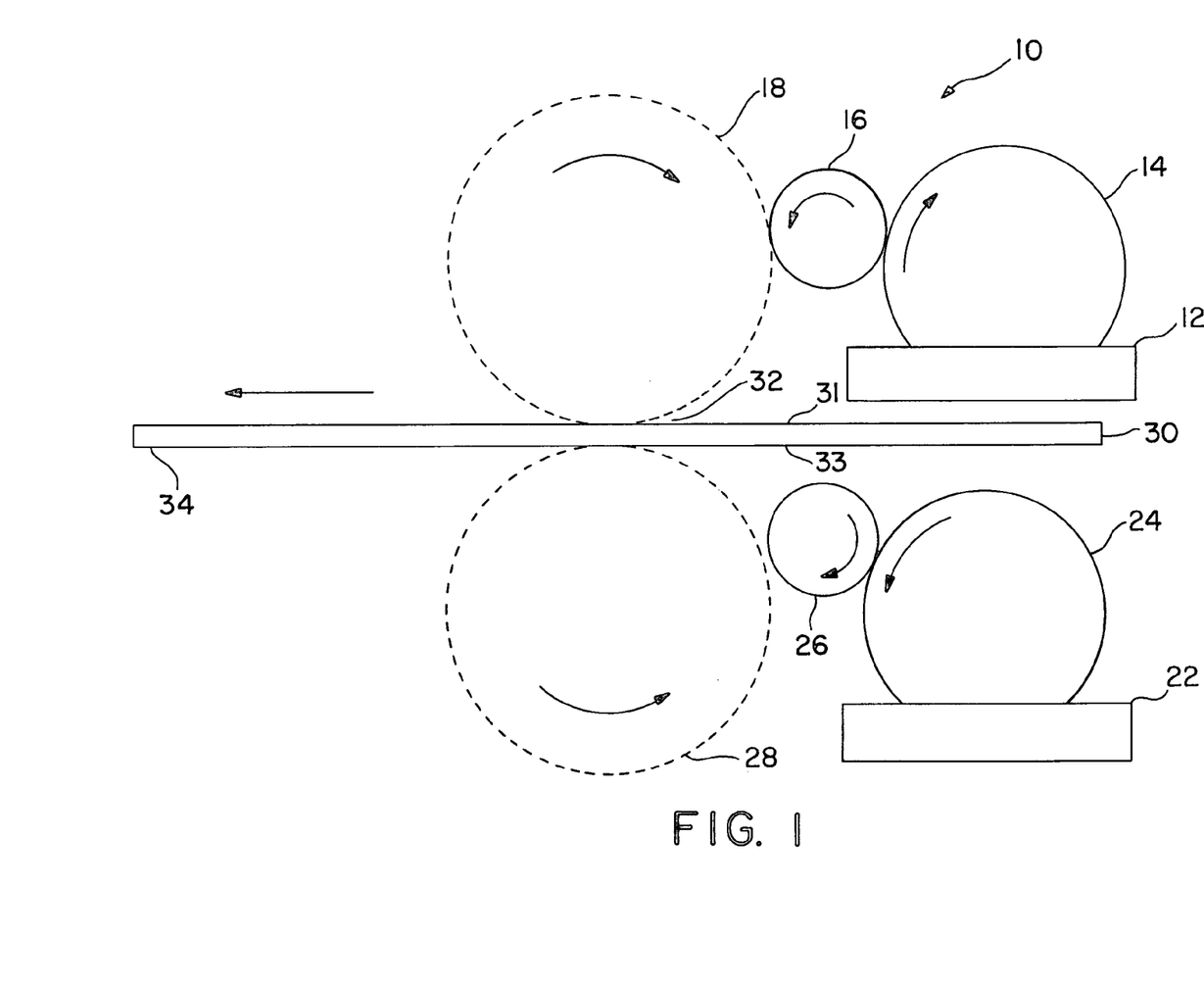
FIG. 1 is a schematic illustration of one embodiment of a process useful for practicing the method of the invention.

FIG. 1 schematically illustrates a point-to-point printing process 10 which can be used to apply first and second superabsorbent polymer precursor compositions at the same corresponding locations on opposing sides of a porous substrate, for instance a fibrous web. A first superabsorbent polymer precursor composition in a holding container 12 is picked up by a sponge roll 14 or other suitable pick-up roll, and is carried to a transfer roll 16 which deposits the first precursor composition on first point-to-point printing roll 18 at spaced apart locations corresponding to a surface pattern on roll 18. A second superabsorbent polymer precursor composition in a holding container 22 is picked up by a sponge roll 24 or other suitable pick-up roll, and is carried to a transfer roll 26 which deposits the second precursor composition on second point-to-point printing roll 28 at spaced-apart locations corresponding to a surface pattern on roll 28.

The surface patterns on point-to-point printing rolls 18 and 28 can be the same, or can be mirror opposites of each other. The gravure printing rolls 18 and 28 rotate in opposite directions at the same surface velocity, defining a nip 32 between the two printing rolls. The movement of the rolls 18 and 28 is synchronized, and the rolls are in register with each other such that the surface patterns on both rolls coincide with each other at the nip 32. A porous substrate 30, which can be a fibrous nonwoven web, passes through the nip 32. The substrate 30 receives the first superabsorbent polymer precursor composition from first gravure roll 18 at a plurality of spaced-apart locations on a first side 31 of substrate 30. The substrate 30 receives the second superabsorbent polymer precursor composition from second gravure roll 28 at the same (corresponding) plurality of spaced-apart locations on a second side 32 of substrate 30.

Because substrate 30 is porous, the first and second superabsorbent polymer precursor compositions are brought together at microdomain locations due to light pressure applied at the nip 32. The first and second precursor compositions chemically react with each other at the microdomain locations to form absorbent structure 34.

Figure 2:
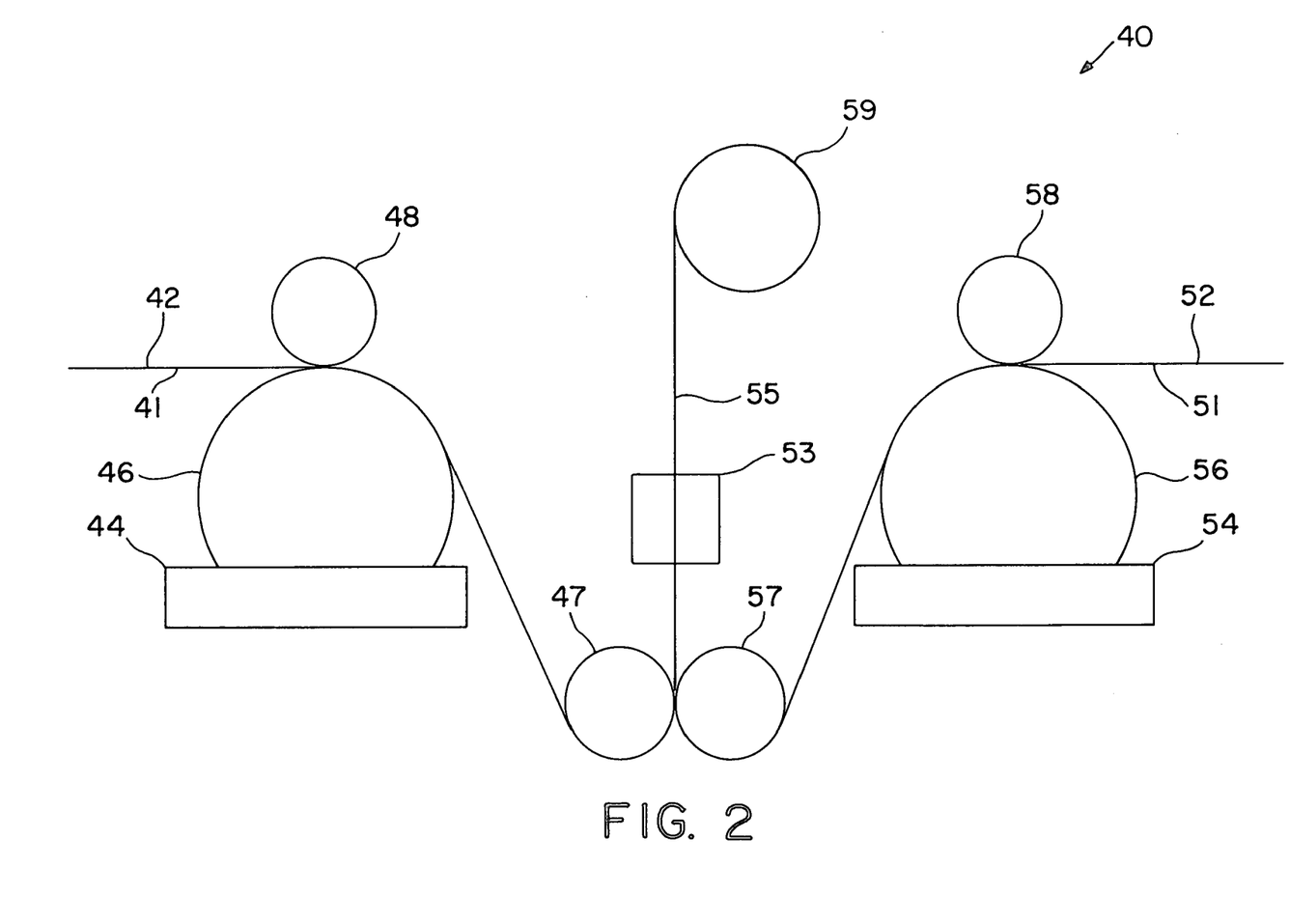
FIG. 2 is a schematic illustration of another embodiment of a process useful for practicing the method of the invention.

FIG. 2 schematically illustrates a gravure printing process 40 which can be used to apply a first superabsorbent polymer precursor composition at spaced-apart locations to one side of a first substrate 42, to apply a second superabsorbent polymer composition at similar spaced locations to one side of a second substrate 52, and to bring the substrates together so that the treated sides of the substrates 42 and 52 contact each other, bringing the first and second superabsorbent polymer precursor compositions together at the same spaced-apart locations. The first superabsorbent polymer precursor composition is picked up by first gravure roll 46 from container 44, and is transferred to a plurality of spaced-apart locations on a first side 41 of substrate 42. The printing occurs as the substrate passes through a nip defined by gravure roll 46 and a smooth (e.g., rubber) anvil roll 48. The second superabsorbent polymer precursor composition is picked up by second gravure roll 56 from container 54, and is transferred to a corresponding plurality of spaced-apart locations on a first side 51 of substrate 52.

The treated surface 41 of substrate 42 and the treated surface 51 of substrate 52 are brought into contact in a nip defined by laminating or embossing rolls 47 and 57. The substrates 42 and 52 are in register so that, when they are brought into contact, the first and second superabsorbent polymer precursor compositions contact each other at the spaced-apart locations. The precursor compositions react to form spaced-apart microdomains of superabsorbent polymer. Oven 53 may aid the reaction. The resulting two-ply absorbent structure 55 can be stored on a wind-up roll 59.

Figure 3A:
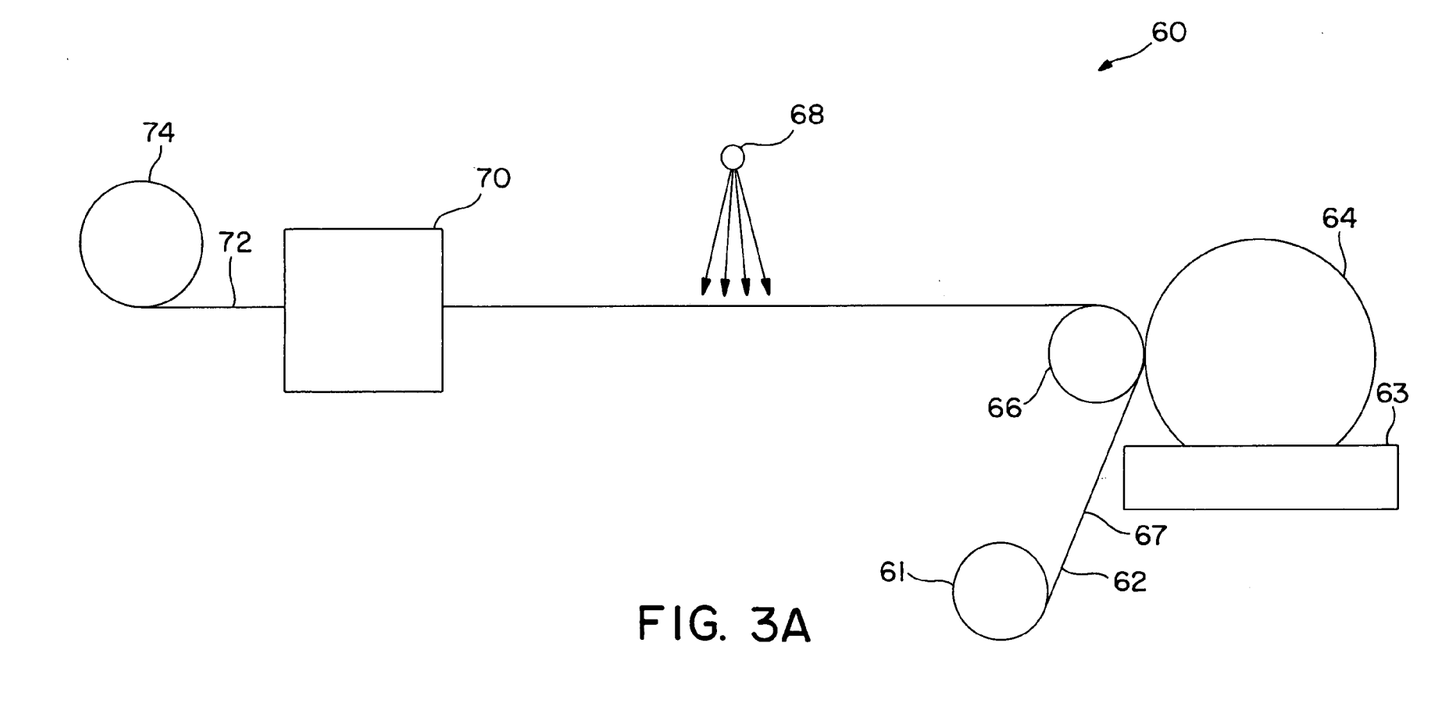
FIG. 3A is a schematic illustration of another embodiment of a process useful for practicing the method of the invention.

In the process 60 of FIG. 3A, a substrate 62 is unwound from roll 61 and is fed to a nip defined by gravure printing roll 64 and smooth (e.g., rubber) anvil roll 66. Gravure roll 64 picks up the first superabsorbent polymer precursor composition from container 63 and transfers it to a first surface 67 of substrate 62, at a plurality of spaced-apart locations corresponding to a surface pattern on gravure roll 64. The second superabsorbent polymer precursor composition is then uniformly sprayed over the entire first surface 67 using a spraying apparatus 68. The first and second superabsorbent polymer precursor compositions contact each other only at the spaced-apart locations where the first precursor composition was applied. The coated substrate 62 passes through an oven 70, and the first and second superabsorbent polymer precursor compositions chemically react at the spaced-apart locations to form microdomains of superabsorbent polymer on or in the substrate 62. The resulting absorbent structure 72 may be stored on a winder roll 74.

Figure 3B:
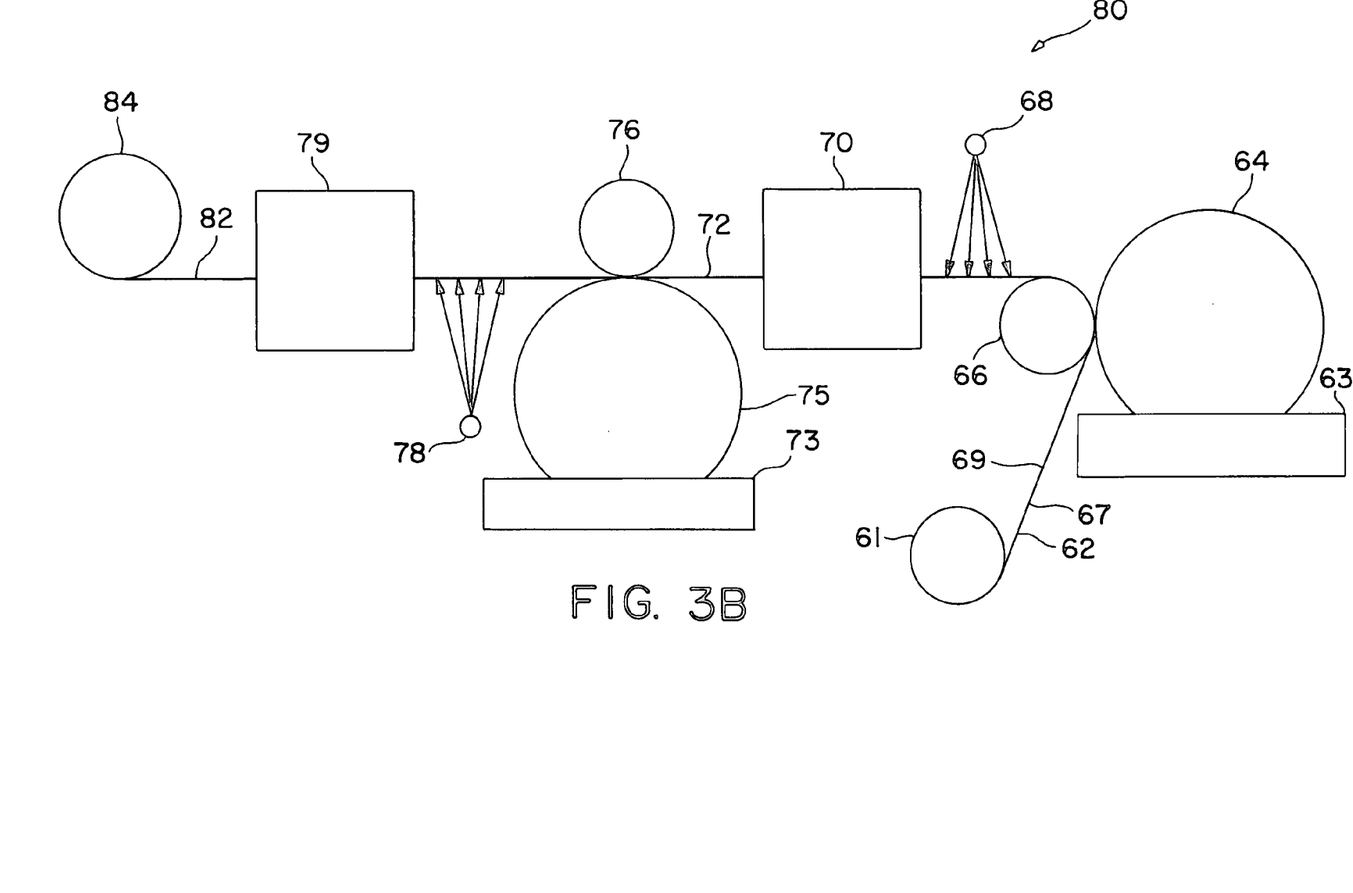
FIG. 3B is a schematic illustration of another embodiment of a process useful for practicing the method of the invention.

The process 80 of FIG. 3B incorporates the process 60 of FIG. 3A with the following additional features. After leaving the oven 70, the absorbent structure 72 is coated on a second surface 69 with the first superabsorbent polymer precursor composition. A second gravure printing roll 75 transfers the first precursor composition from container 73 and applies it to second surface 69 at a plurality of spaced-apart locations. The second superabsorbent polymer precursor composition is then uniformly sprayed over the entire second surface 69 using spraying apparatus 78. The first and second superabsorbent polymer precursor compositions contact each other on the second surface only at the spaced-apart locations where the second precursor composition was applied. The coated substrate then passes through a second oven 79, and the first and second superabsorbent polymer precursor compositions chemically react at the spaced locations to form additional microdomains of superabsorbent polymer on or in the substrate 62. The resulting absorbent structure 82 may be stored on a winder roll 84.

The first and second precursor compositions chemically react with each other at the spaced-apart locations to form discrete, spaced-apart microdomains of superabsorbent material. When the substrate is a fibrous web, the microdomains of superabsorbent material may be formed on or around the fibers in the substrate, and adhering to the fibers. The superabsorbent microdomains may have an average diameter of about 10 to about 1000 microns when dry and unswollen, particularly about 50 to about 800 microns, particularly about 100 to about 500 microns. Individual microdomains maybe spaced-apart from adjacent microdomains by an average of about 30 to about 3000 microns when dry and unswollen, particularly about 150 to about 2500 microns, particularly about 300 to about 1500 microns, between the closest adjacent edges. The spacing-between the microdomains ensures that the absorbent structure will have sufficient liquid intake and distribution rates even when many of the superabsorbent domains are swollen to their maximum capacities. The pattern, size, depth of penetration and spacing of the microdomains may vary depending on the design and operating conditions of the printing device. Because of the in situ polymerization, the locations of the microdomains are fixed and the microdomains of superabsorbent polymer adhere firmly to the substrate at the fixed locations.

Process conditions, feed rates, and the like should also be tailored to produce the desired composition for the absorbent structure. For example, when the substrate is a fibrous web, the process conditions and feed rates may be tailored to produce an absorbent structure having the following compositions:

| | Composition, % By Weight | | |
|---|---|---|---|
| | Hydrophilic Fibers | Superabsorbent Polymer Formed In Situ | Thermoplastic Fibers |
| Broad | 25–99 | 1–75 | 0–74 |
| Intermediate | 35–80 | 15–65 | 0–45 |
| Narrow | 40–70 | 20–50 | 10–30 |

Examples of superabsorbent polymers which may be formed in situ include without limitation the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), and mixtures and copolymers thereof. Additional superabsorbent materials (some of which maybe separately formed and added to the substrate) may also be included in the absorbent structure. Additional superabsorbents include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Known processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

The absorbent structure of the invention is useful in a wide variety of absorbent articles, particularly as an absorbent core material in personal care absorbent articles, medical absorbent articles, tissue and towel articles. Personal care absorbent articles include diapers, training pants, swim wear, absorbent underpants, baby wipes, adult incontinence products, feminine hygiene products and the like. Medical absorbent articles include medical absorbent garments, drapes, gowns, bandages, wound dressings, underpads, wipes, and the like. Tissue and towel absorbent articles include facial and bathroom tissue, paper towels such as kitchen towels, away-from-home towels, wet wipes, and the like.

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

We claim:

1. A method of making an absorbent structure, comprising the steps of:
   providing a first superabsorbent polymer precursor composition including a superabsorbent-forming monomer, a crosslinking agent and a reducing agent;
   providing a second superabsorbent polymer precursor composition including a superabsorbent-forming monomer, a crosslinking agent and an oxidizing agent;
   providing a pre-formed substrate;
   adding one of the first and second superabsorbent polymer precursor compositions to the substrate at a plurality of spaced-apart locations;
   adding the other of the first and second superabsorbent polymer precursor compositions to the substrate; and
   chemically reacting the first and second superabsorbent polymer precursor compositions at the plurality of spaced-apart locations to form a plurality of discrete, spaced-apart microdomains of superabsorbent polymer adhering to the substrate;
   wherein the first and second superabsorbant polymer precursor compositions are not combined with each other before being added to the substrate.

2. The method of claim 1, wherein the other of the first and second superabsorbent polymer precursor compositions is added to the substrate at the plurality of spaced-apart locations.

3. The method of claim 1, wherein at least one of the first and second superabsorbent polymer precursor compositions is added using a printing process.

4. The method of claim 2, wherein each of the first and second superabsorbent polymer precursor compositions is added using a printing process.

5. The method of claim 3, wherein the printing process comprises a gravure printing process.

6. The method of claim 4, wherein the printing process comprises a gravure printing process.

7. The method of claim 1, wherein the first and second superabsorbent polymer precursor compositions are added to the substrate at the same time.

8. The method of claim 1, wherein the first and second superabsorbent polymer precursor compositions are added to the substrate at different times.

9. The method of claim 1, wherein the spaced-apart locations have an average diameter of about 10 to about 1000 microns and an average spacing of about 30 to about 3000 microns.

10. The method of claim 1, wherein the spaced-apart locations have an average diameter of about 50 to about 800 microns and an average spacing of about 150 to about 2500 microns.

11. The method of claim 1, wherein the spaced-apart locations have an average diameter of about 100 to about 500 microns and an average spacing of about 300 to about 1500 microns.

12. The method of claim 1, wherein the monomer in the first superabsorbent polymer precursor composition and the monomer in the second superabsorbent polymer precursor composition each comprises a compound selected from the group consisting of aliphatic unsaturated monocarboxylic acids and their salts, methacrylic acids and their salts, unsaturated dicarboxylic acids and their salts, and combinations thereof.

13. The method of claim 1, wherein the monomer in the first superabsorbent polymer precursor composition and the monomer in the second superabsorbent polymer precursor composition each comprises a compound selected from the group consisting of acrylic acid and its salts, methacrylic acid and its salts, and combinations thereof.

14. The method of claim 1, wherein the crosslinking agent in the first superabsorbent polymer precursor composition and the crosslinking agent in the second superabsorbent polymer precursor composition each comprises a compound selected from the group consisting of $N_1N'$-methylenebis(meth)acrylamide, (poly)ethylene glycol, di(meth)acrylate, polyglycidyl ethers, and combinations thereof.

15. The method of claim 1, wherein the reducing agent comprises a compound selected from the group consisting of sodium sulfite, sodium hydrogensulfite, sodium metabisulfite, tertiary amines, diamines, L-ascorbic acid, alkali metal salts of L-ascorbic acid, and combinations thereof.

16. The method of claim 1, wherein the oxidizing agent comprises a compound selected from the group consisting of hydrogen peroxide, potassium bromate, N-bromosuccinimide, ammonium persulfate, sodium persulfate, potassium persulfate, hydroperoxides, secondary cerium salts, permanganates, chlorites, hypochlorites, and combinations thereof.

17. A method of making an absorbent structure, comprising the steps of:
   providing a fibrous web substrate including about 25 to about 100% by weight hydrophilic fibers and zero to about 75% by weight thermoplastic fibers;
   adding a first superabsorbent polymer precursor composition including ay least a monomer to the fibrous web at a plurality of discrete, spaced-apart locations;
   adding a second superabsorbent polymer precursor composition including at least a monomer to the fibrous web at the plurality of discrete, spaced-apart locations; and
   chemically reacting the first and second superabsorbent polymer precursor compositions at the plurality of locations to form a plurality of discrete, spaced-apart microdomains of superabsorbent polymer adhering to the fibrous web;
   wherein the first and second superabsorbant polymer precurser compositions are not combined with each other before being added to the fibrous web.

18. The method of claim 17, wherein the first superabsorbent polymer precursor composition comprises a monomer, a crosslinking agent and a reducing agent, and the second superabsorbent polymer precursor composition comprises a monomer, a crosslinking agent and an oxidizing agent.

19. The method of claim 17, wherein the fibrous web substrate comprises about 50 to about 100% by weight hydrophilic fibers and zero to about 50% by weight thermoplastic fibers.

20. The method of claim 17, wherein the fibrous web substrate comprises about 60 to about 90% by weight hydrophilic fibers and about 10 to about 40% by weight thermoplastic fibers.

21. The method of claim 17, wherein the first and second superabsorbent polymer precursor compositions are added to the fibrous web at the same time.

22. The method of claim 17, wherein the first and second superabsorbent polymer precursor compositions are added to the fibrous web at different times.

23. The method of claim 17, wherein the first and second superabsorbent polymer precursor compositions are added to the fibrous web using a gravure printing process.

24. The method of claim 17, wherein the first and second superabsorbent polymer precursor compositions are added to the fibrous web using a screen printing process.

25. A method of making an absorbent structure, comprising the steps of:

providing a first superabsorbent polymer precursor composition including a monomer, a crosslinking agent and a reducing agent;

providing a second superabsorbent polymer precursor composition including a monomer, a crosslinking agent and an oxidizing agent; and chemically reacting the first and second superabsorbent polymer precursor compositions at a plurality of spaced-apart locations on or in a substrate to provide a plurality of discrete, spaced-apart microdomains of superabsorbent polymer adhered to the substrate;

wherein the first and second superabsorbant polymer precurser compositions are not combined with each other apart from the substrate.

26. The method of claim 25, wherein the microdomains of superabsorbent polymer have an average diameter of about 10 to about 1000 microns and an average spacing of about 30 to about 3000 microns.

27. The method of claim 25, wherein the microdomains of superabsorbent polymer have an average diameter of about 100 to about 500 microns and an average spacing of about 300 to about 1500 microns.

* * * * *